United States Patent
Leybovich

(10) Patent No.: US 6,739,196 B2
(45) Date of Patent: May 25, 2004

(54) CLEANLINESS EVALUATION IN SPUTTER TARGETS USING PHASE

(75) Inventor: Alexander Leybovich, Hilliard, OH (US)

(73) Assignee: Tosoh SMD, Inc., Grove City, OH (US)

( * ) Notice: Subject to any disclaimer, the term of this patent is extended or adjusted under 35 U.S.C. 154(b) by 0 days.

(21) Appl. No.: 10/275,060

(22) PCT Filed: May 4, 2001

(86) PCT No.: PCT/US01/14403

§ 371 (c)(1),
(2), (4) Date: Oct. 31, 2002

(87) PCT Pub. No.: WO01/86282

PCT Pub. Date: Nov. 15, 2001

(65) Prior Publication Data

US 2003/0226402 A1 Dec. 11, 2003

Related U.S. Application Data

(60) Provisional application No. 60/203,568, filed on May 11, 2000.

(51) Int. Cl.⁷ ................................................. G01N 29/04
(52) U.S. Cl. ............................................ 73/620; 73/598
(58) Field of Search .......................... 73/597, 598, 600, 73/620, 618, 619, 627

(56) References Cited

U.S. PATENT DOCUMENTS

| | | |
|---|---|---|
| 2,790,216 A | 4/1957 | Hunter |
| 4,054,173 A | 10/1977 | Hickam |
| 4,568,007 A | 2/1986 | Fishler |

(List continued on next page.)

FOREIGN PATENT DOCUMENTS

| | | |
|---|---|---|
| EP | 0 211 401 B1 | 5/1992 |
| EP | 0 418 846 B1 | 2/1995 |
| EP | 0 665 193 A2 | 8/1995 |
| EP | 0 467 659 B1 | 3/1996 |
| EP | 0 412 843 B1 | 5/1996 |
| EP | 0 561 161 B1 | 4/1997 |
| WO | WO 97/30348 | 8/1997 |
| WO | WO 99/64854 | 12/1999 |
| WO | WO 00/15863 | 3/2000 |

OTHER PUBLICATIONS

Freitag, W.O. et al., "Diode Sputtering of Cermet Films," *Symposium on Deposition of Thin Films by Sputtering*, University of Rochester and Consolidated Vacuum Corporation, Rochester, NY, Jun. 1967, pp. 92–96.

Robinson, J.E. et al., "Models for Chunk Sputtering," *Journal of Nuclear Materials*, 1976, vol. 63, pp. 432–437, North–Holland Publishing Company.

Eernisse, E.P. et al., "Role of Integrated Lateral Stress in Surface Deformation of He–Implanted Surfaces," *Journal of Applied Physics*, Jan. 1, 1977, vol. 48, No. 1, pp. 9–17, American Institute of Physics.

Roth, R.M. et al., "Spatial Dependence of Particle Light Scattering in an RF Silane Discharge," *Appl. Phys. Letter*, Feb. 1, 1985, vol. 46, No. 3, pp. 253–255, American Institute of Physics.

(List continued on next page.)

*Primary Examiner*—Hezron Williams
*Assistant Examiner*—Nashmiya Fayyaz
(74) *Attorney, Agent, or Firm*—Wegman, Hessler & Vanderburg

(57) ABSTRACT

An improved method and apparatus for non-destructive cleanliness evaluation in sputter targets using radio frequency waveform phase change and amplitude detection is disclosed. The apparatus acquires phase change and amplitude for a plurality of data points. The method disclosed for characterizing the sputter target material (52) employs the phase change and amplitude magnitude data for calculating cleanliness factors and generating pareto histograms.

13 Claims, 5 Drawing Sheets

U.S. PATENT DOCUMENTS

| | | | |
|---|---|---|---|
| 5,160,388 | A | 11/1992 | Legresy et al. |
| 5,369,063 | A | 11/1994 | Gee et al. |
| 5,406,850 | A | 4/1995 | Bouchard et al. |
| 5,559,614 | A | 9/1996 | Urbish et al. |
| 5,636,681 | A | 6/1997 | Sulzer et al. |
| 5,738,767 | A | 4/1998 | Coad et al. |
| 5,827,409 | A | 10/1998 | Iwata et al. |
| 5,887,481 | A | 3/1999 | Leroy et al. |
| 5,943,559 | A | 8/1999 | Maeda |
| 5,955,673 | A | 9/1999 | Leroy et al. |
| 5,989,782 | A | 11/1999 | Nishiki et al. |
| 6,001,227 | A | 12/1999 | Pavate et al. |
| 6,017,779 | A | 1/2000 | Miyasaka |
| 6,019,657 | A | 2/2000 | Chakvorty et al. |
| 6,020,946 | A | 2/2000 | Callegari et al. |
| 6,057,557 | A | 5/2000 | Ichikawa |
| 6,139,701 | A | 10/2000 | Pavate et al. |
| 6,439,054 | B1 * | 8/2002 | Gore et al. .................. 73/620 |
| 6,487,910 | B1 * | 12/2002 | Leybovich .................. 73/620 |
| 2002/0184970 | A1 * | 12/2002 | Wickersham et al. ......... 75/412 |

OTHER PUBLICATIONS

Wehner, G.K., "Cone Formation as a Result of Whisker Growth on Ion Bombarded Metal Surfaces," *J. Vac. Sci. Techol.*, Jul./Aug. 1985, A 3 (4), pp. 1821–1835, American Vacuum Society.

Spears, K.G. et al., "Particle Distributions and Laser–Particle Interactions in aN RF Discharge of Silane," *IEEE Transactions on Plasma Science*, Apr. 1986, vol. PS–14, No. 2, pp. 179–187, IEEE.

Selwyn, G.S. et al., "*In Situ* Diagnostic Studies of Plasma–Generated Particulate Contamination," *J. Vac. Sci. Technol.*, Jul./Aug. 1989, A 7, (4) pp. 2758–2765, American Vacuum Society.

Anderson, H.M. et al., "Particulate Generation in Silane / Ammonia RF Discharges," *J. Applied Physics*, May 1, 1990, vol. 67, No. 9, pp. 3999–4011, American Institute of Physics.

Jellum, G.M. et al, "Particulates in Aluminum Sputtering Discharges," *J. Appl. Phys.*, May 15, 1990, vol. 67 No. 10, pp. 6490–6496, American Institute of Physics.

Selwyn, G.S. et al., "*In situ* Plasma Contamination Measurements by HeNe Laser Light Scattering: A Case Study," *J. Vac. Sci. Techol.*, May / Jun. 1990, A 8, (3) pp. 1726–1731, American Vacuum Society.

Selwyn, G.S. et al., "Particle Trapping Phenomena in Radio Frequency Plasmas," *Appl.Phys. Letter*, Oct. 29, 1990, vol. 57, No. 18 pp. 1876–1878, American Institute of Physics.

Akari, K. et al., "Reduction in Macroparticles During the Deposition of TiN Films Prepared by Arc Ion Plating," *Surface and Coatings Technology*, 1990, 43/44, pp. 312–323, Elsevier Sequoia, The Netherlands.

Barnes, M.S. et al., "Transport of Dust Particles in Glow–Discharge Plasmas," *Physical Review Letters*, Jan. 20, 1992, vol. 68, No. 3, pp. 313–316, The American Physical Society.

Smadi, M.M. et al., "Particle Contamination on a Silicon Substrate in a $SF_6$/ Ar Plasma," *J. Vac. Sci. Techol.*, Jan. /Feb. 1992, B 10, (1) pp. 30–36, American Vacuum Society.

Yoo, W.J. et al., "Kinetics of Particle Generation in Sputtering and Reactive Ion Etching Plasmas," *Appl. Phys. Letter*, Mar. 2, 1992, vol. 60, No. 9, pp. 1073–1075, American Institute of Physics.

Logan, J.S. et al., "Study of Particle Emission in Vacuum from Film Deposits," *J. Vac. Sci. Techol.*, Jul./Aug. 1992, A 10, (4) pp. 1875–1878, American Vacuum Society.

Goree J. et al., "Particulate Release from Surfaces Exposed to a Plasma," *J. Vac. Sci. Techol.*, Nov./Dec. 1992, A 10, (6) pp. 3540–3544, American Vacuum Society.

Anderson, L., "A New Technique for Arc Control in DC Sputtering," *Society of Vacuum Coaters 35th Annual Technical Conference Proceedings*, 1992, pp. 325–329.

Nadel, S.J. et al., "Enhanced Chromium First Surface Mirrors," *Society of Vacuum Coaters, 35th Annual Technical Conference Proceedings*, 1992, pp. 365–369.

Scholl, R.A., "A New Method of Handling Arcs and Reducing Particulates in DC Plasma Processing," *Society of Vacuum Coaters 37th Annual Technical Conference Proceedings*, 1994, pp. 312–315, Advanced Energy Industries, Inc.

Lee, F. et al., "Detecting and Reducing Particles for LPCVD Silicon Nitride Deposition," *Microcontamination*, Mar. 1994, vol. 12, pp. 33–37, 76–77.

Bailey, R.S. et al., "Particle Emission from $Al_2O_3$ Doped Aluminum Targets During Sputtering Deposition," *VMIC Conference, ISMIC*, Jun. 7–8, 1994, p. 317.

Takahashi, K.M. et al., "Current Capabilities and Limitations of *In Situ* Particle Monitors in Silicon Processing Equipment," *J. Vac. Sci. Technol.*, Nov./Dec. 1996, A 14, (6) pp. 2983–2993, American Vacuum Society.

Selwyn, G.S. et al., "Particle Contamination Formation in Magneton Sputtering Processes," *J. Vac. Sci. Technol*, Jul./Aug. 1997, A 15 (4), pp. 2023–2028, American Vacuum Society.

Monteiro, O.R. et al., "Vacuum–Arc–Generated Macroparticles in the Nanometer Range," *IEEE Transactions on Plasma Science*, Aug. 1999, vol. 27, No. 4, pp. 1030–1033, IEEE.

Abburi, M. et al., "Low–Defect Target Metallurgy Development for sub–0.18$\mu$m Al–based Interconnects," *Solid State Technology*, Dec. 1999, vol. 42, pp. 55–58, Solid State Technology.

Danovich, D. et al., "Sputtering Issues for Flat–Panel Displays," *Information Display*, (Nov. 1995), pp. 26–27, 30–31.

Foster, H.I. et al., "A Modular Approach to Sputter coating of Flat Panel Displays," *Society of Vacuum Coaters 35th Annual Technical Conference (1992)* pp. 357–361.

Von Guntherschulze, A., *Z. Physik*, (1993) 86,778.

* cited by examiner

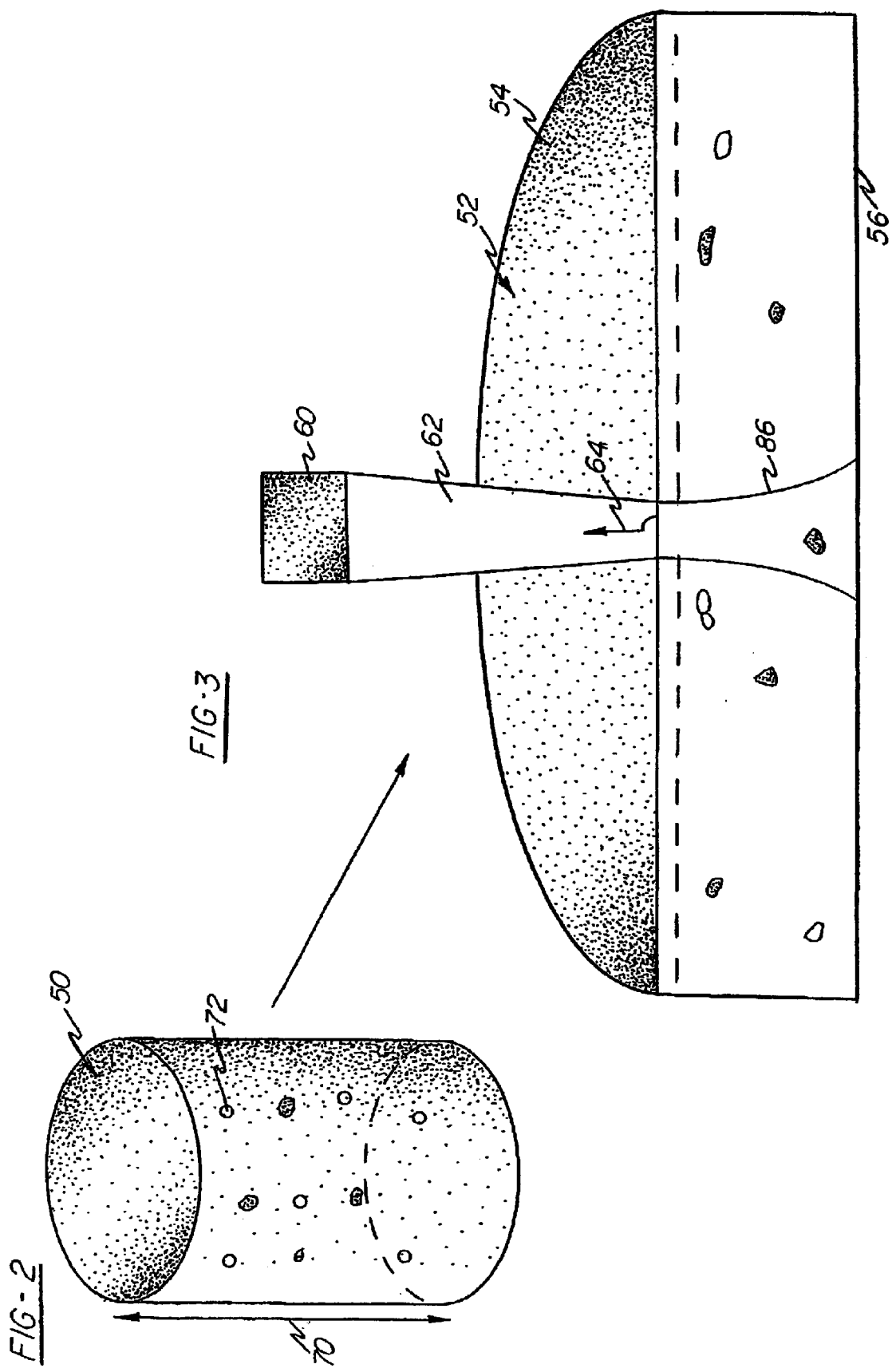

CLEANLINESS EVALUATION IN SPUTTER TARGETS USING PHASE

CROSS-REFERENCE TO RELATED APPLICATIONS

Priority filing benefit of (1) International PCT application PCT/US01/14403 filed May 4, 2001, and published under PCT 21(2) in the English language and (2) U.S. provisional application Serial No. 60/203,568 filed May 11, 2000.

FIELD OF THE INVENTION

This invention relates to non-destructive testing methods and apparatus for identifying types of intrinsic flaws in metallic sputter target materials and, more particularly, non-destructive methods and apparatus for identifying and counting of solid inclusions using radio frequency echo waveform phase change detection.

BACKGROUND OF THE INVENTION

Cathodic sputtering is widely used for depositing thin layers or films of materials from sputter targets onto desired substrates such as semiconductor wafers. Basically, a cathode assembly including a sputter target is placed together with an anode in a chamber filled with an inert gas, preferably argon. The desired substrate is positioned in the chamber near the anode with a receiving surface oriented normal to a path between the cathode assembly and the anode. A high voltage electric field is applied across the cathode assembly and the anode.

Electrons ejected from the cathode assembly ionize the inert gas. The electrical field then propels positively charged ions of the inert gas against a sputtering surface of the sputter target. Material dislodged from the sputter target by the ion bombardment traverses the chamber and deposits on the receiving surface of the substrate to form the thin layer or film.

One factor affecting the quality of the layer or film produced by a sputtering process is the "cleanliness" of the material from which the sputter target is made. The term "cleanliness" is widely used in the semiconductor industry, among others, to characterize high purity and ultra high purity materials. In common practice, "cleanliness" refers to the degree of material internal purity. Such impurities may be present, for example, as traces of foreign elements in distributed or localized form in the sputter target material. Cleanliness is usually measured in units of particles per million ("ppm") or particles per billion ("ppb") which define a ratio between the number of contaminant atoms and the total number of atoms sampled.

Since the cleanliness of the material from which a sputter target is made affects the quality of layers of films produced using that target, it is obviously desirable to use relatively clean materials in fabricating sputter targets. This implies a need in the art for non-destructive techniques for selecting sputter target blanks of suitable cleanliness to produce high quality sputter targets. Known destructive test methods, such as glow discharge mass spectroscopy and LECO techniques, are not suitable for this purpose.

Another factor affecting the quality of the layer or film produced by a sputtering process is the presence of "flaws" in the sputter target material. As used herein, the term "flaws" refers to microscopic volumetric defects in the sputter target material, such as inclusions, pores, cavities and micro-laminations. However, not all the flaws are "alike" in their degrading effect on sputter performance. Some types of flaws, for example, micro-cavities or shrinkage porosity cause relatively "mild" degrading effect on sputter performance while the others, such as dielectric inclusions, cause a serious disturbance in the sputter process. Therefore, there exists a corresponding need in the art for a non-destructive technique which identifies and separately counts different kinds of flaws which may exist in sputter target materials.

FIG. 1 illustrates a prior art non-destructive ultrasonic "flaw" detection method for characterizing aluminum and aluminum alloy sputter target materials. The technique illustrated in FIG. 1 is similar to that suggested in Aluminum Pechiney PCT Application No. PCT/FR96/01959 for use in classifying aluminum or aluminum alloy blanks suitable for fabricating sputter targets based on the size and number of internal "decohesions" detected per unit volume of the blanks.

The prior art technique of FIG. 1 employed a pulse-echo method performed on a test sample 10 having a planar upper surface 12 and a parallel planar lower surface 14. In accordance with this technique, a focused ultrasonic transducer 16 irradiated a sequence of positions on the upper surface 12 of the test sample 10 with a single, short-duration, high-frequency ultrasound pulse 18 having a frequency of at least 5 MHz, and preferably 10–50 MHz. The ultrasonic transducer 16 then switched to a sensing mode and detected a series of echoes 20 induced by the ultrasound pulse 18.

One factor contributing to these echoes 20 was scattering of sonic energy from the ultrasound pulse 18 by flaws 22 in the test sample 10. By comparing the amplitudes of echoes induced in the test sample 10 with the amplitudes of echoes induced in reference samples (not shown) having compositions similar to that of the test sample 10 and blind, flat-bottomed holes of fixed depth and diameter, it was possible to detect and count flaws 22 in the test sample 10.

The number of flaws detected by the technique of FIG. 1 had to be normalized in order to facilitate comparison between test samples of different size and geometry. Conventionally, the number of flaws was normalized by volume—that is, the sputter target materials were characterized in units of "flaws per cubic centimeter." The volume associated with the echoes 20 from each irradiation of the test sample 10 was determined, in part, by estimating an effective cross-section of the pulse 18 in the test sample 10.

A portion of the scattered energy is attenuated by the material making up the test sample 10. Furthermore, since the single flaw sizes of interest, which range from approximately 0.04 mm to 0.8 mm, are of same range with the wavelength of ultrasound in metals (for example, the wavelength of sound in aluminum for the frequency range of 10 MHz to 50 MHz is 0.6 mm to 0.12 mm respectively), the pulse 18 has a tendency to refract around the flaws 22, which reduces the scattering intensity.

Another factor detracting from the ability of the transducer 16 to detect the sonic energy scattered by the flaws 22 is the physical nature of the substance of the flaw or more accurately a degree of acoustic impedance mismatch at the flaw—matrix material boundary. The impedance mismatch directly affects the reflection and transmission characteristics of ultrasound at the phase boundaries. The reflection coefficient of ultrasound beam at matrix-to-flaw boundary can be expressed by the simplified expression: $R=(I_2-I_1)/(I_2+I_1)$, where $I_2$ is an acoustic impedance of the flaw material, and $I_1$ is an acoustic impedance of the matrix material. The simple analysis of this formula allows us to derive several important conclusions. At first, if acoustic impedance of the flaw $I_2$ is less than the acoustic impedance of the matrix $I_1$, then the R coefficient becomes negative. The negativity of the R can be translated as a change in the phase of the acoustic pulse waveform on 180°. For example, if the flaw is the gas-filled or vacuumed (shrinkage) void with the acoustic impedance equal to 0.93 g/cm²-sec(×10⁶) (air) or below (vacuum), then the phase of the ultrasound pulse waveform is changed on 180° at the boundary. At second, if the flaw is a gas filled or vacuumed void in the aluminum matrix with the acoustic impedance of 17.2 g/cm²-sec(×10⁶), then the reflection coefficient value is close to the unity or 100% and the amplitude of the reflected signal is the only function of the relationship between flaw size and the ultrasound beam focal spot size. At third, if the flaw comprises a solid particle, for example, an alumina inclusion with the acoustic impedance of 39.6 g/cm²-sec(×10⁶), which exceeds the acoustic impedance of the aluminum matrix more than two times (17.2 g/cm² sec(×10⁶)), the ultrasound waveform does not experience the phase inversion at the flaw boundary, and for alumina inclusion the reflection coefficient does not exceed 39.5% of the amplitude of the impinging pulse (if the wave interference effect is not considered). In this case, the amplitude of the reflected signal is the function of two variables, firstly, the relationship between flaw size and the beam focal spot size, and secondly, the degree of acoustic impedance mismatch at flaw-to-matrix boundary.

Therefore, the final conclusion is that the void-like flaw and alumina inclusion of same size reflect the ultrasound energy quite differently. In addition to the waveform phase inversion, the amplitude of the reflected signal from the void-like flaw is at least two times higher than for the alumina particle inclusion. Hence, the detectability of alumina inclusions is generally poorer than the detectability of void-like flaws, and if the phase information for reflected signal is not extracted simultaneously with the amplitude information, the testing results can be misleading caused by misinterpretation of the actual larger alumina particle with the smaller void-like flaw and vice versa.

Another factor detracting from the ability of the transducer 16 to detect the sonic energy scattered by the flaws 22 is the noise generated by scattering of the pulse 18 at the boundaries between grains having different textures. In fact, the texture-related noise can be so great for high-purity aluminum having grain sizes on the order of several millimeters that small flaws within a size range of approximately 0.05 mm and less cannot be detected. Larger grain sizes reduce the signal-to-noise ratio for the sonic energy scattered by the flaws when compared to the noise induced by the grain boundaries.

Other factors affecting the sensitivity and resolution of the technique of FIG. 1 include the pulse frequency, duration and waveform; the degree of beam focus and the focal spot size; the coupling conditions (that is, the efficiency with which the sonic energy travels from the transducer 16 to the test sample 10); and the data acquisition system parameters.

One major drawback to the technique of FIG. 1 is an inability of the technique to distinguish between different sorts of flaws, particularly between void-like flaws and solid particle inclusions, such as alumina particles. This technique, which relies only on the echo amplitude measurements, confirms only the physical existence of the flaw. Its physical nature and actual size are not properly revealed and derived only on the basis of the flaw type assumption. If the internal "decohesions" (void-like defects) are the only defects in the target material, then the technique as referred in the method (FIG. 1) is able to detect and size defects adequately. However, in reality the internal "decohesions" as referred in the method (FIG. 1), are the fraction of plurality of defect types which may exist in the target material. For example, the metallographic evaluation revealed also aluminum oxide particles in the aluminum for sputter targets. Therefore, the technique as referred in the method (FIG. 1) is unable to distinguish and to differentiate between pluralities of flaw types since the waveform phase change information remains not revealed.

Thus, there remains a need in the art for non-destructive techniques for characterizing sputter target materials having different pluralities of flaw types. There also remains a need for a technique that separately compares the target intrinsic volumetric cleanliness for the specific groups of flaws such as void-like flaws (cavities, microlaminations, "decohesions") and solid inclusions.

One imaging technique implemented by Sonix, Inc. (8700 Morrisette Dr., Springfield, Va. 22152) in a FlexSCAN-C C-scanning uses a phase gating method which detects the phase inversion in the waveform at the matrix-to-flaw boundary. The technique uses a "Texas Instruments" phase inversion algorithm (licensed to SONIX, Inc.). The technique maps the flaws on a two-dimensional sample image only if the 180° phase change is detected. Therefore, this technique is limited to detection and mapping void-like defects when the impedance is changed from higher to lower at the flaw boundary. For sputter target applications however, it is absolutely necessary to detect and identify the alumina particle-inclusions, and the phase inversion technique used by the Sonix, Inc. does not work in this case since the waveform does not change its phase at the flaw boundary.

There also remains a need for a technique that separately detects and sizes specific alumina particle-inclusions.

SUMMARY OF THE INVENTION

These needs and others are addressed by a non-destructive method for characterizing a sputter target material comprising the steps of sequentially irradiating a test sample of the sputter target material with sonic energy at a plurality of positions on a surface of the sample; detecting echoes induced by the sonic energy; discriminating texture-related backscattering noise from the echoes to obtain non-rectified radio frequency echo waveform signals; monitoring non-rectified echo waveform signals for the 180° waveform phase inversion, comparing the non-rectified echo waveform signals with said at least one of each: phase inverting and phase non-inverting reference values, to detect void-like and particle-like flaw data points separately and no-flaw data points; counting the flaw data points for the each flaw type separately as well as all together to determine a total flaw count $C_{FT(TOTAL)}$; $C_{FI(with\ phase\ inversion)}$, flaw count without phase inversion $C_{FN(without\ phase\ inversion)}$, counting the flaw data points and the no-flaw data points to determine a total number of data points $C_{DP}$ and calculating a total cleanliness factor $F_{CT}=(C_{FT}/C_{DP})\times 10^6$ as well as cleanliness factors $F_{CI}=(C_{FI}/C_{DP})\times 10^6$ and $F_C=(C_{FN}/C_{DP})\times 10^6$ for each sort of flaws separately.

Unlike the prior art method described earlier, the method of the present invention provides a characterization of the sputter target material by separately identifying and counting void-like and particle-like flaws. A partition of cleanliness factor for components associated with different kinds of flaws tunes up the rejection criteria more precisely by identifying and sizing the flaws of different kind.

Unlike the Sonix, Inc. method, the method of the present invention provides a characterization of both the waveform phase inverting and phase non-inverting flaws. Therefore, there is a smaller risk to miss the waveform phase non-inverting flaws which are of a primary concern for sputter target applications.

Although the cleanliness factor technique provides a useful characterization of the sputter target material, more information can be provided by means of a histogram. More specifically, the sputter target test method may be characterized by defining a plurality of amplitude bands for each type (waveform inverting and non-inverting) of flaws; measuring said modified amplitude signals to determine modified amplitude signal magnitudes; comparing said modified amplitude signal magnitudes with said plurality of amplitude bands to form subsets of said modified amplitude signals; counting said subsets of modified amplitude signals to determine a plurality of modified amplitude signal counts, each modified amplitude signal count of said plurality of amplitude signal counts corresponding to one of said amplitude bands of said plurality of amplitude bands; and constructing a pareto histogram, combining individual histograms for both flaw classes, relating said modified signals counts to said plurality of amplitude bands. Since the histogram does not attempt to directly map the locations of flaws along the surface of the sputter target material, it does not suffer from the scaling problems.

Most preferably, the test sample is compressed along one dimension, such as by rolling or forging, and then irradiated by sonic energy propagating transversely (that is, obliquely or, better yet, normally) to that dimension. This has the additional effect of flattening and widening of certain flaws (aluminum oxide film clusters and voids) in the material. The widening of the flaws, in turn, increases the intensity of the sonic energy scattered by the flaws and reduces the likelihood that the sonic energy will refract around the flaws.

These methods for characterizing sputter target materials may be used in processes for manufacturing sputter targets. As noted earlier, the cleanliness of a sputter target and particularly cleanliness from non-phase inverting flaws is the primary factor determining the quality of the layers or films produced by the target. By shaping only those sputter target blanks having cleanliness factors or histograms meeting certain reference criteria to form sputter targets, and rejecting blanks not meeting those criteria, one improves the likelihood that the sputter targets so manufactured will produce high quality layers or films.

Therefore, it is one object of the invention to provide non-destructive methods for characterizing sputter target materials. Other objects of the invention will be apparent from the follow description, the accompanying drawings and the appended claims.

BRIEF DESCRIPTION OF THE DRAWINGS

FIG. 2 is a perspective view illustrating an especially preferred test sample, prior to compressing, used for cleanliness characterization in accordance with the invention;

FIG. 3 is a schematic view illustrating an especially preferred method of ultrasonic cleanliness characterization, utilizing a compressed version of the test sample as shown in FIG. 2, in accordance with the invention;

DETAILED DESCRIPTION OF THE PREFERRED EMBODIMENTS

Figure 1:
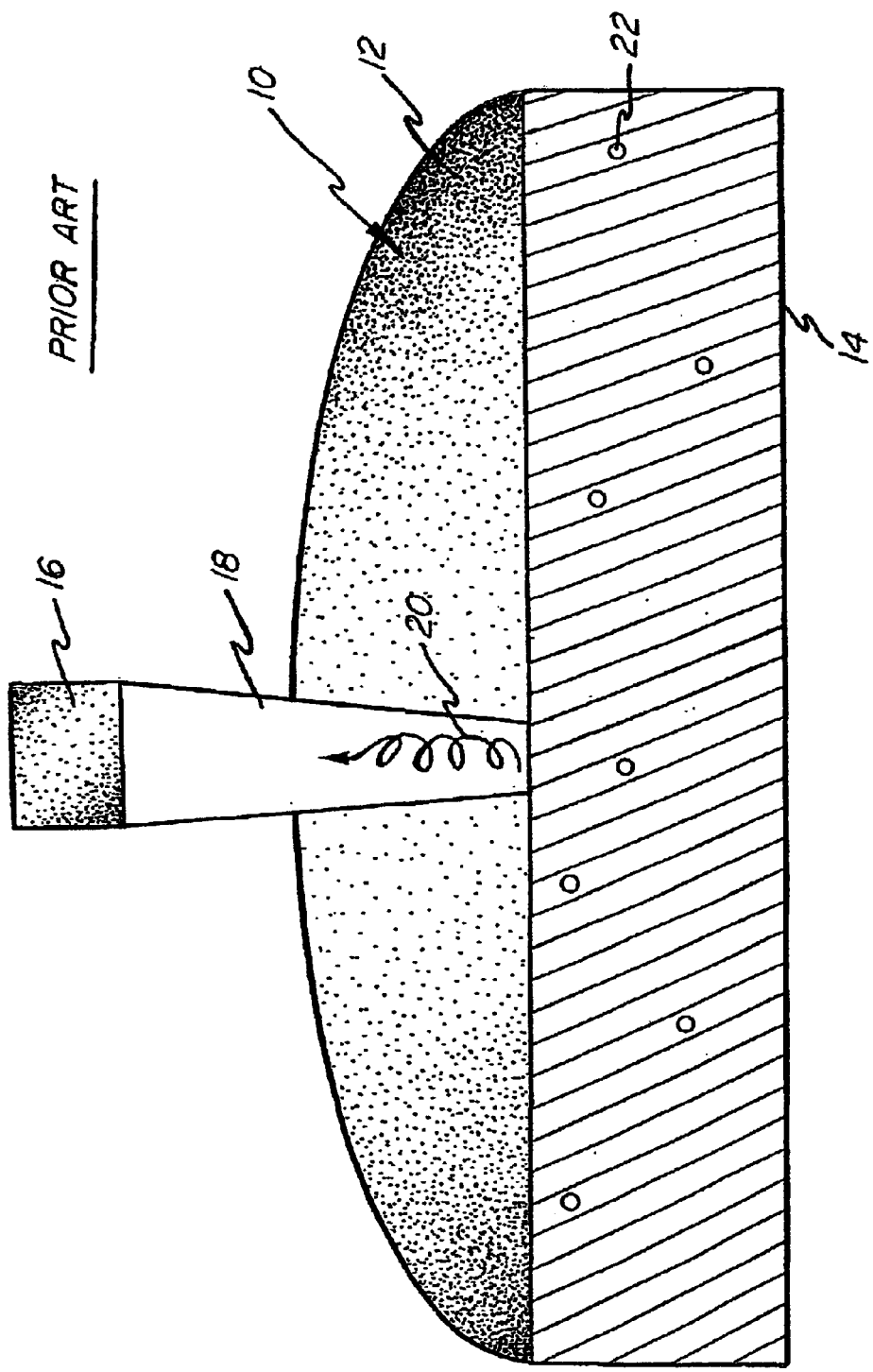
FIG. 1 is a schematic view illustrating of prior art method of ultrasonic texture analysis.

FIG. 3 illustrates an especially preferred method for sorting of flaws and characterizing the cleanliness of sputter target material. In accordance with this method, a cylindrical sample 50 of the sputter target material (which preferably comprises metal or a metal alloy) is compressed or worked to produce a disc-shaped test sample 52 having a planar upper surface 54 and a planar lower surface 56 approximately parallel to the upper surface 54. Thereafter, a focused ultrasonic transducer 60 is positioned near the upper surface 54. The transducer 60 irradiates the upper surface 54 of the test sample 52 with a single, short-duration, MHz frequency range pulse of sonic energy 62. The transducer 60 subsequently detects an echo 64 induced in the test sample 52 by the pulse of sonic energy 62. The transducer 60 converts the echo into an electrical radio frequency signal (not shown), which is processed to retrieve the waveform phase and maximum amplitude information.

More specifically, the sample 50, as shown in FIG. 2, first is compressed along a dimension 70 to form the disc-shaped test sample 52 as shown in FIG. 3. Preferably, the sample 50 is compressed by forging or rolling of the sample 50, followed by diamond cutting to prepare the planar surfaces 54 and 56. The reduction in the dimension 70 may be anywhere between 0% to 100%. The compression of the sample 50 flattens and widens certain flaws 72 to increase their surface area normal to the dimension 70.

Figure 4:
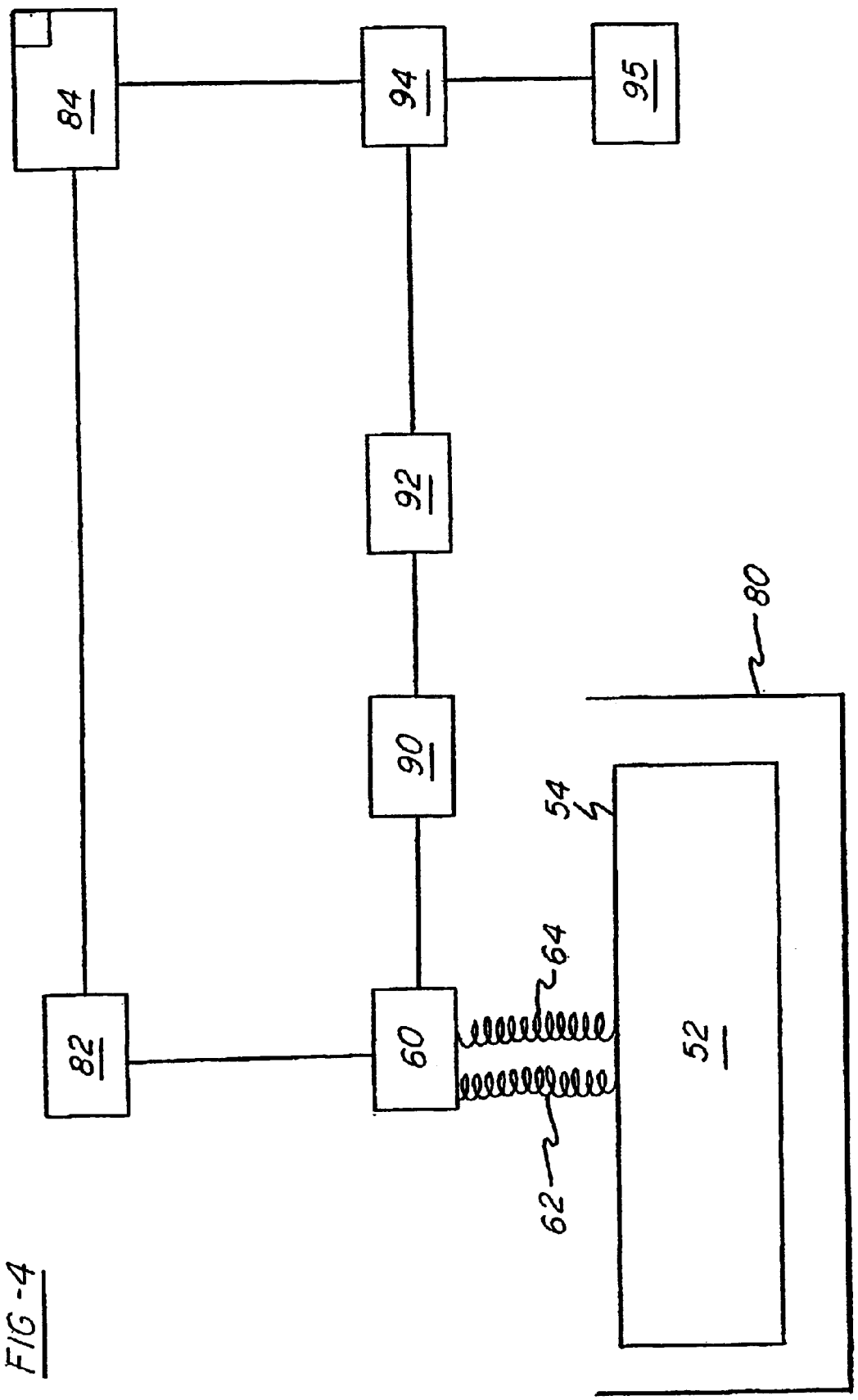
FIG. 4 is a schematic view of a test apparatus for carrying out the method of FIG. 3.

As illustrated in FIG. 4, the test sample 52 is immersed in deionized water (not shown) in a conventional immersion tank 80. The transducer 60 is mounted on a mechanical X-Y scanner 82 in electrical communication with a controller 84 such as a PC controller. The controller 84 is programmed in a conventional manner to induce the mechanical X-Y scanning unit 82 to move the transducer 60 in a raster-like stepwise motion across the upper surface 54 of the test sample 52.

Again, with respect to FIG. 3, the presently preferred transducer 60 is sold by ULTRAN USA under the designation WS50-10P4.5. This is a long focal length piezoelectric transducer having a fixed focal length of 114 mm (in water). At a peak frequency of approximately 9.15 MHz with 8 MHz (−6 dB) bandwidth, the transducer produces a pulse of sonic energy 62 having a focal zone (−6 dB) of approximately 21 mm in aluminum and a focal spot 0.8–0.9 mm in diameter.

Most preferably, the upper surface 54 of the sample 52 has a width or diameter on the order of approximately 28 cm. Data acquisition steps of approximately 0.9 mm in both the "x"-direction and the "y"-direction permit the detection of 0.25 mm flat bottom holes at a detection level of −6 dB without exposure area overlap. One thereby irradiates approximately 100,000 test points on the upper surface 54.

Most preferably, the transducer 60 is oriented so that the pulse of sonic energy 62 propagates through the deionized water (not shown) in the immersion tank 80 and strikes the test sample 52 approximately normal to the upper surface 54. Furthermore, the transducer 60 is preferably spaced from the upper surface 54 such that the pulse of sonic energy 62 is focused on a zone 86 of the test sample 52 between approximately 3 mm and 24 mm below the upper surface 54.

The pulse of sonic energy 62 interacts with the sample 52 to induce echoes 64, which then propagate back through the deionized water (not shown) to the transducer 60 approximately 60 μsec after the pulse of sonic energy 62 is sent.

Turning back to FIG. 4, an especially preferred echo acquisition system includes a low noise receiver comprising a low noise gated preamplifier 90; a low noise linear amplifier 92 with a set of calibrated attenuators, a 12-bit (2.44 mV/bit) analog-to-digital converter 94 and digital oscilloscope 95 connected with receiver analog output. When sufficient time has elapsed for the echoes to arrive at the transducer 60, the controller 84 switches the transducer 60 from a transmitting mode to a gated electronic receiving mode. The echoes 64 are received by the transducer 60 and converted into an RF electric signal (not shown). The RF signal is amplified by the preamplifier 90 and by the low noise linear amplifier 92 to produce modified amplitude signal and displayed on the screen of oscilloscope 95 to extract waveform phase information. The modified amplitude signal then is digitized by the analog-to-digital converter 94 before moving on to the controller 84. The analog-to-digital conversion is performed so as to preserve amplitude information from the analog modified amplitude signal.

Flaws of given nature (void-like or alumina inclusions) are determined by monitoring for waveform phase inversion using digital oscilloscope 95. Flaws of given sizes are detected by comparing the digitized modified amplitude signals obtained from the sample 52 with reference values (or calibration values) derived from tests conducted on reference samples (not shown) having compositions similar to those of the test sample 10 and either blind, flat-bottomed holes of fixed depth and diameter or alumina particles of given size artificially imbedded into reference sample material.

The especially preferred PC controller 84 controls the data acquisition process. An especially preferred software package used in connection with the data acquisition system is available from Structural Diagnostics, Inc. under the designation SDI-5311 Winscan.

The PC controller 84 is also programmed to calculate the total cleanliness factor and the cleanliness factors for the sorted flaws characterization the material of the samples 50, 52. More precisely, it is programmed to discriminate texture-related backscattering noise and to distinguish "void-like flaw data points from the alumina particle-like flaw data points." The PC controller 84 maintains a count of the flaw data points detected during the testing of a test sample 52 to determine a flaw count "$C_{FT}$," "$C_{FI}$," "$C_{FM}$."

The PC controller 84 also is programmed to distinguish "no-flaw data points," that is, digitized modified amplitude signals representing amplitudes which, after comparison with the reference values, indicate the absence of flaws.

The PC controller also determines a total number of data points "$C_{DP}$," that is, the sum of the flaw count CF and the number of no-flaw data points. Although the total number of data points could be determined by maintaining counts of the flaw data points and the no-flaw data points, it is preferably determined by counting the total number of positions "$C_I$" along the upper surface 54 at which the test sample 52 is irradiated by the transducer 60 and subtracting the number of digitized RF signals "$C_N$" which the data acquisition circuitry was unable, due to noise or other causes, to identify as either flaw data points or no-flaw data points. (Alternatively, the "noise count" $C_N$ may be described as the number of positions along the upper surface 54 at which neither a flaw data point nor a no-flaw data point is detected.)

Having determined the flaw counts $C_{FT}$, $C_{FI}$, $C_{FN}$, and the total number of data points $C_{DP}$, the PC controller is programmed to calculate the cleanliness factor $F_C=(C_{FT}/C_{DP})\times 10^6$, $F_{CN}=(C_{FI}/C_{DP})\times 10^6$, $C_N=(C_{FN}/C_{DP})\times 10^6$ to characterize the material comprising the samples 50, 52. Unlike the prior art "flaws per cubic centimeter," the magnitude of the cleanliness factor is not dependent on any estimate of pulse cross-sectional area. Since the cleanliness factor is normalized by the dimensionless coefficient $C_{DP}\times 10^{-6}$ rather than by volume, it is more closely related to ppm and ppb units than are units of "flaws per cubic centimeter."

The preparation of a suitable program for determining the cleanliness factor in accordance with the invention as disclosed herein is within the ordinary skill in the art and requires no undue experimentation.

Another way in which to characterize the material comprising the samples 50, 52 is by determining the size distribution of flaws in the test sample 52. More specifically, one may characterize the cleanliness of the sample 52 by defining amplitude bands or ranges; comparing the amplitudes represented by the digitized modified amplitude signal for certain types of flaws (phase inverting and phase non-inverting) with the amplitude bands to form subsets of the modified amplitude signals; counting these subsets of modified amplitude signals to determine a modified amplitude signal counts for each amplitude band and for each type of flaws; and constructing a pareto histogram relating the modified signal counts to said plurality of amplitude bands. Since the amplitudes represented by the digitized modified amplitude signals for each type of flaws are related to the sizes of flaws detected in the sample 52, the histogram provides an indication of the flaw size distribution in the sample 52.

Figure 5:
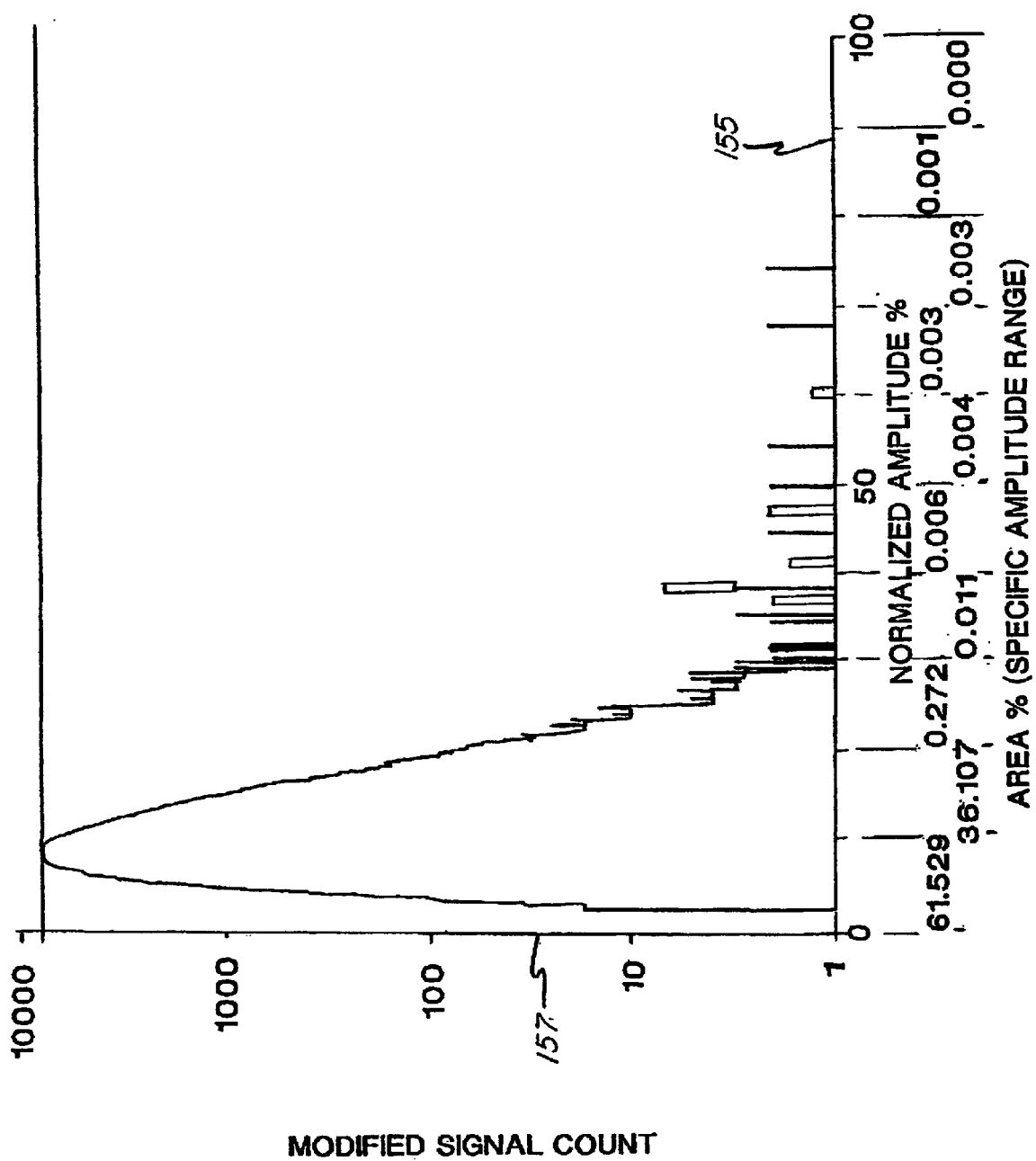
FIG. 5 is a histogram characterizing a relatively "clean" Al-0.5 wt % Cu material in accordance with an especially preferred form of the invention.
Figure 6:
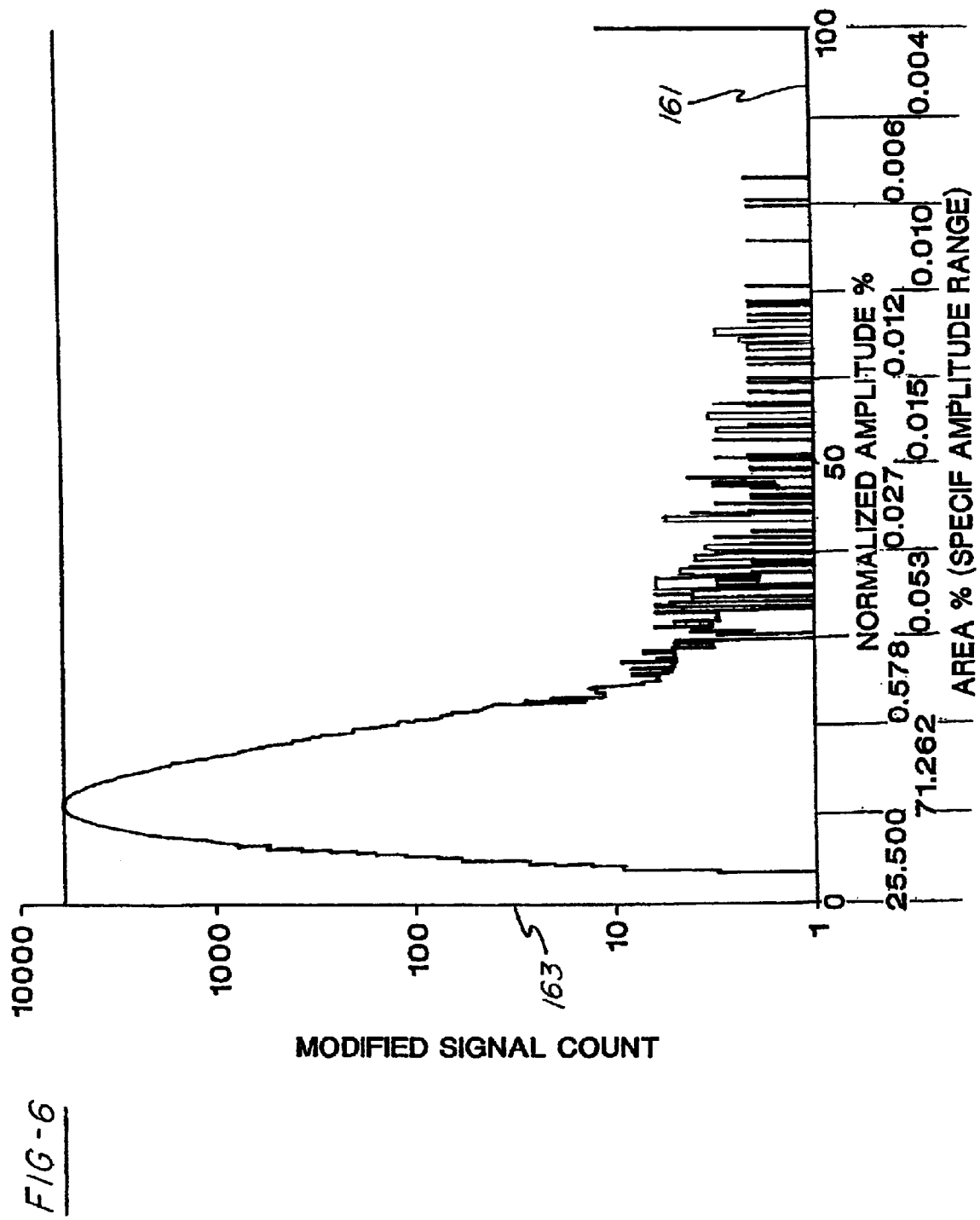
FIG. 6 is a histogram characterizing a less "clean" Al-0.5 wt % Cu material in accordance with the especially preferred form of the invention.

Turning now to FIGS. 5 and 6, there may be seen pareto histograms characterizing two Al-0.5 wt % Cu alloy sputter target materials having orthorhombic textures and grain sizes in the range of 0.08 mm to 0.12 mm. The material of FIG. 5 was "cleaner" than that of FIG. 6; the material of FIG. 5 had a cleanliness factor $C_{FT}$ of 250 and $C_{FN}$ of 100 while the material of FIG. 6 had a cleanliness factor $C_F$ of 1,200 and $C_{FN}$ of 300. It is important to emphasize that for sputtering applications to have a lower $C_{FN}$ value is more important than to have the lower $C_{FT}$ value. The zone of flaw monitoring was located within a gate of seven microsecond duration with a gate delay of 1 microsecond.

The abscissa 155 of the pareto histogram of FIG. 5 represents the amplitude normalized as a percentage of the echo amplitude induced in a reference sample having a 0.8 mm blind, flat-bottomed hole. The ordinate 157 in FIG. 5 represents the modified signal counts for each amplitude, expressed on a logarithmic scale. The echo amplitude threshold for the flaw counting was set to 12% since, as established experimentally, the texture-related echo amplitude did not exceed 10% for all aluminum alloys tested. The abscissa 161 and ordinate 163 of the histogram of FIG. 6 were scaled similarly.

The histograms of FIGS. 4 and 5 represent an improvement over prior art imaging techniques in that the distribution of flaw sizes may be represented without having to represent flaw sizes relative to the surface area of the test sample (not shown).

The preparation of a suitable program for plotting histograms such as those shown in FIGS. 5 and 6 in accordance with the invention as disclosed herein is within the ordinary skill in the art and requires no undue experimentation. Either the cleanliness factor or histograms such as those shown in FIGS. 5 and 6 may be used in a process for manufacturing sputter targets. As noted earlier, the cleanliness of a sputter target is one factor determining the quality of the layers or films produced by the target. By shaping only those sputter target blanks having cleanliness factors and particularly $C_{FN}$ less than reference cleanliness factors, or having histograms with selected columns or areas less than reference values, to form sputter targets, and rejecting blanks not meeting those criteria, one improves the likelihood that the sputter targets so manufactured will produce high quality layers or films.

While the method herein described, and the form of apparatus for carrying this method into effect, constitute a preferred embodiment of this invention, it is to be understood that the invention is not limited to this precise method and form of apparatus, and that changes may be made in either without departing from the scope of the invention, which is defined in the appended claims.

What is claimed is:

1. A non-destructive method for characterizing sputter target material, comprising the steps:
   a) obtaining a reference value for waveform phase inverting flaws and a reference value for waveform phase non-inverting flaws utilizing a reference sample;
   b) irradiating a test sample of said sputter target material sequentially with sonic energy at a plurality of positions along a surface of said test sample;
   c) detecting radio frequency echo waveforms induced by said sonic energy;
   d) discriminating texture-related backscattering noise from said echo waveforms to obtain a radio frequency echo waveform signal;
   e) monitoring said radio frequency echo waveform signal for 180° waveform phase inversion;
   f) comparing the radio frequency echo waveform signal associated with each of said plurality of positions with said waveform phase inverting reference value and said waveform phase non-inverting reference value and obtaining individual data points associated with a void-like flaw, a particle-like flaw and no-flaw;
   g) counting the data points associated with waveform phase inverting flaws, waveform phase non-inverting flaws, and no-flaws to determine a flaw count associated with waveform phase inversion flaws $C_{FI}$, a flaw count associated with waveform phase non-inversion flaws $C_{FN}$, a total flaw count $C_{FT}$, and a total number of data points $C_{DP}$; and
   h) calculating a total cleanliness factor $F^{CT}=(C_{FT}/C_{DP})\times 10^6$, a cleanliness factor associated with phase inversion flaws $F_{CI}=(C_{FI}/C_{DP})\times 10^6$ and a cleanliness factor associated with phase non-inversion flaws $F_C=(C_{FN}/C_{DP})\times 10^6$.

2. A non-destructive method for characterizing sputter target material as in claim 1, wherein said reference sample comprises blind, flat-bottomed, holes of fixed depth and diameter.

3. A non-destructive method for characterizing sputter target material as in claim 1, wherein said reference sample comprises alumna particles of given size artificially imbedded.

4. A non-destructive method for characterizing sputter target material as in claim 1, wherein said test sample is a cylindrical portion of said sputter target material.

5. A non-destructive method for characterizing sputter target material as in claim 4, wherein said cylindrical portion is formed into a disc-shaped test sample.

6. A non-destructive method for characterizing sputter target material as in claim 5, wherein said disc-shaped test sample is formed by rolling said cylindrical portion.

7. A non-destructive method for characterizing sputter target material as in claim 5, wherein said disc-shaped test sample is formed by forging said cylindrical portion.

8. A non-destructive method for characterizing sputter target material as in claim 5, wherein said disc-shaped test sample comprises first and second planar surfaces.

9. A non-destructive method for characterizing sputter target material as in claim 8, wherein said first and second planar surfaces are prepared by diamond cutting.

10. A non-destructive method for characterizing sputter target material as in claim 1, wherein said sonic energy is generated by a transducer.

11. A non-destructive method for characterizing sputter target material as in claim 10, further comprising the step:
    immersing said test sample in deionized water within an immersion tank and orienting said transducer such that said sonic energy propagates through said deionized water striking said test sample substantially normal to an upper surface of said test sample.

12. A non-destructive method for characterizing sputter target material as in claim 10, wherein:
    said transducer is piezoelectric and comprises a fixed focal length in water of approximately 114 mm, a peak frequency of approximately 9.15 MHz with approximately 8 MHz (−6 dB) bandwidth; and
    said transducer produces a pulse having a focal zone (−6 dB) of approximately 21 mm in aluminum and a focal spot 0.8–0.9 mm in diameter.

13. A non-destructive method for characterizing sputter target material as in claim 12, wherein:
    said test sample comprises an upper surface with a width on the order of approximately 28 cm; and
    obtaining said data points in raster-like stepwise motion in steps approximately 0.9 mm in both a x-direction and a y-direction over the entire said upper surface.

* * * * *